(12) United States Patent
Aoki et al.

(10) Patent No.: US 9,064,419 B2
(45) Date of Patent: Jun. 23, 2015

(54) DRIVER CONDITION ASSESSMENT DEVICE

(75) Inventors: Hirofumi Aoki, Susono (JP); Kiyoto Hanita, Susono (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 101 days.

(21) Appl. No.: 14/114,058

(22) PCT Filed: Apr. 23, 2012

(86) PCT No.: PCT/JP2012/060879
§ 371 (c)(1),
(2), (4) Date: Dec. 11, 2013

(87) PCT Pub. No.: WO2012/147699
PCT Pub. Date: Nov. 1, 2012

(65) Prior Publication Data
US 2014/0091916 A1    Apr. 3, 2014

(30) Foreign Application Priority Data
Apr. 28, 2011    (JP) .................................. 2011-101589

(51) Int. Cl.
*B60Q 1/00*    (2006.01)
*G08G 1/16*    (2006.01)
(Continued)

(52) U.S. Cl.
CPC *G08G 1/16* (2013.01); *G08B 21/06* (2013.01); *G08G 1/166* (2013.01); *A61B 5/18* (2013.01);
(Continued)

(58) Field of Classification Search
CPC .......... G08B 21/06; B60Q 1/525; B60Q 1/52; B60Q 1/28; B60Q 9/008; G08G 1/16; B60K 28/06

USPC ...................... 340/435, 436, 575, 903, 573.1; 701/301, 70
See application file for complete search history.

(56) References Cited

U.S. PATENT DOCUMENTS

| | | | | |
|---|---|---|---|---|
| 6,014,601 | A * | 1/2000 | Gustafson | 701/45 |
| 8,725,403 | B2 * | 5/2014 | Aoki et al. | 701/301 |
| 2005/0126841 | A1 | 6/2005 | Isaji et al. | |
| 2009/0132109 | A1 | 5/2009 | Galley et al. | |

FOREIGN PATENT DOCUMENTS

| | | |
|---|---|---|
| JP | 11-034773 A | 2/1999 |
| JP | 2005-173929 A | 6/2005 |

(Continued)

*Primary Examiner* — Vernal Brown
*Assistant Examiner* — Hongmin Fan
(74) *Attorney, Agent, or Firm* — Sughrue Mion, PLLC

(57) ABSTRACT

A driver condition determination device determines whether a driver of a host vehicle has degraded consciousness. A main component for distribution of an accelerating operation condition with respect to proximity when tailgating a preceding vehicle is analyzed (S16), all data is origin-shifted (S18), and the accelerating operation condition of the driver when the driver has consciousness is created as a normal traveling model (S20). The likelihood of the accelerating operation condition, a likelihood average, a likelihood variance, and a likelihood threshold value are calculated (S22 to S26), and it is determined whether the likelihood of a current driving operation is lower than the likelihood threshold value (S28). When the likelihood is lower than the likelihood threshold value, the driver is determined as being in degraded consciousness. Since the likelihood threshold value is calculated for determination on the basis of data when the driver has consciousness, an erroneous determination of degraded consciousness due to difference in driver operation characteristics is suppressed.

3 Claims, 4 Drawing Sheets

(51) Int. Cl.
*G08B 21/06* (2006.01)
*A61B 5/18* (2006.01)
*B60K 28/06* (2006.01)
*B60W 40/08* (2012.01)

(52) U.S. Cl.
CPC ............... *B60K 28/066* (2013.01); *B60K 28/06* (2013.01); *B60W 2040/0827* (2013.01); *B60W 2540/10* (2013.01); *B60W 2540/26* (2013.01); *B60W 2550/30* (2013.01); *B60W 2550/302* (2013.01); *B60W 2550/308* (2013.01)

(56) References Cited

FOREIGN PATENT DOCUMENTS

| | | | |
|---|---|---|---|
| JP | 2007-182226 | A | 7/2007 |
| JP | 2008-140118 | A | 6/2008 |
| JP | 2008-542935 | A | 11/2008 |
| JP | 2009-145951 | A | 7/2009 |
| JP | 2011-060207 | A | 3/2011 |
| JP | 2011-216058 | A | 10/2011 |

\* cited by examiner

*Fig.2*
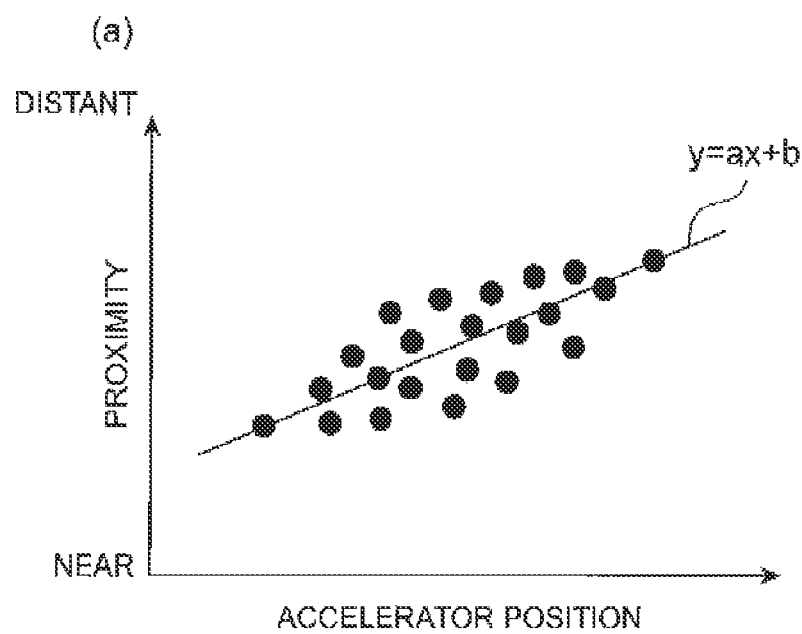
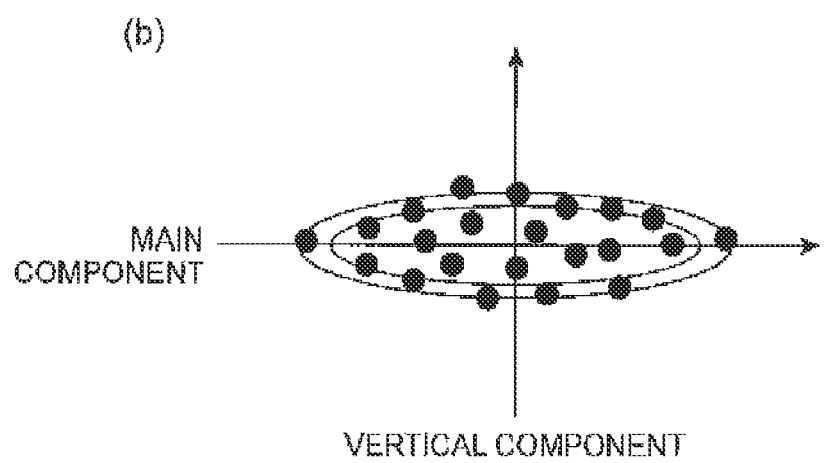

DRIVER CONDITION ASSESSMENT DEVICE

CROSS REFERENCE TO RELATED APPLICATIONS

This is a National Stage of International Application No. PCT/JP2012/060879 filed Apr. 23, 2012, claiming priority based on Japanese Patent Application No. 2011-101589 filed Apr. 28, 2011, the contents of all of which are incorporated herein by reference in their entirety.

TECHNICAL FIELD

The present invention relates to a driver condition determination device that determines degraded consciousness of a vehicle driver.

BACKGROUND ART

In the related art, a technique that detects a predetermined driving operation of a driver, and checks the condition of the driver or awakens the driver has been proposed as a technique that determines degraded consciousness of a vehicle driver. For example, Patent Literature 1 discloses a driver condition determination device that determines the awakeness degree of a driver in consideration of the presence or absence of a preceding vehicle to enhance the determination accuracy.

CITATION LIST

Patent Literature

[Patent Literature 1] Japanese Unexamined Patent Application Publication No. 2005-173929
[Patent Literature 2] PCT Japanese Translation Patent Publication No. 2008-542935
[Patent Literature 3] Japanese Unexamined Patent Application Publication No. 11-034773

SUMMARY OF INVENTION

Technical Problem

However, in such a technique, there is a problem that the degraded consciousness of the driver cannot be accurately determined in a predetermined driving operation. Specifically, in a case where the degraded consciousness of the driver is determined on the basis of only proximity to a preceding vehicle such as change in a distance from the preceding vehicle or change in a relative speed with respect to the preceding vehicle, since a determination threshold value for the proximity is constant regardless of the driver or a traveling environment, it may be determined that a certain driver does not have degraded consciousness in a case where the driver performs a driving operation to tailgate a preceding vehicle while having consciousness, whereas it may be determined that a different driver has degraded consciousness even though the driver performs a driving operation to tailgate a preceding vehicle in consciousness. Thus, in a case where the determination threshold value for the degraded consciousness of the driver is constant as mentioned above, an alarm may be unnecessarily output to a driver who is not in degraded consciousness. Hence, there is still plenty of room for improvement in the determination accuracy of the degraded consciousness.

Accordingly, an object of the invention is to provide a driver condition determination device that enhances the determination accuracy of degraded consciousness of a driver in consideration of a driving operation characteristic of the driver in a case where a host vehicle tailgates a preceding vehicle.

Solution to Problem

That is, according to an aspect of the invention, there is provided a driver condition determination device that determines whether a driver of a vehicle has degraded consciousness, including an operation condition detecting section that detects an accelerating operation condition of the driver corresponding to the proximity of the vehicle to a preceding vehicle that is positioned in front of the vehicle and a degraded consciousness determining section that determines that the driver has the degraded consciousness when a gap between the accelerating operation condition of the driver detected by the operation condition detecting section and a normal accelerating operation condition exceeds a preset value.

According to this configuration, the operation condition detecting section detects the normal accelerating operation condition corresponding to the proximity to the preceding vehicle, and the degraded consciousness determining section determines that the driver has the degraded consciousness when the gap from the normal accelerating operation condition exceeds the preset value. Accordingly, it is possible to grasp a characteristic of the driving operation of the driver when a host vehicle tailgates the preceding vehicle, and to determine the degraded consciousness in consideration of the characteristic. Thus, it is possible to suppress an unnecessary alarm from being output to a driver that is not in the degraded consciousness, and thus, it is possible to enhance the determination accuracy of the degraded consciousness of the driver.

Further, the driver condition determination device according to this aspect of the invention may further include a likelihood calculating section that calculates the likelihood of the accelerating operation condition of the driver and the preset value as a likelihood threshold value on the basis of the proximity to the preceding vehicle and a distribution state of the accelerating operation condition, and the degraded consciousness determining section may determine that the driver has the degraded consciousness when the likelihood of the accelerating operation condition of the driver is lower than the likelihood threshold value.

According to this configuration, a distribution of the accelerating operation condition of the driver with respect to the proximity is generated, and the likelihood and the likelihood threshold value of the accelerating operation condition of the driver are calculated from the distribution. Accordingly, it is possible to model the characteristic of the accelerating operation condition of the driver when the host vehicle tailgates the preceding vehicle, and to reliably detect a case where the accelerating operation condition of the driver is not believable.

Further, in the driver condition determination device according to this aspect of the invention, the likelihood calculating section may calculate the likelihood and the likelihood threshold value using a mixed normal distribution.

According to this configuration, the likelihood calculating section calculates the likelihood and the likelihood threshold value using the mixed normal distribution. Accordingly, it is possible to accurately model the accelerating operation condition with respect to the proximity, and to enhance the determination accuracy of the degraded consciousness of the driver.

Advantageous Effects of Invention

According to the invention, since the normal accelerating operation condition when the host vehicle tailgates the preceding vehicle is calculated for each driver and the degraded consciousness of the driver is determined on the basis of the gap from the normal accelerating operation condition, it is possible to perform the determination in consideration of the characteristic of the driving operation of the driver when the host vehicle tailgates the preceding vehicle, and to determine the degraded consciousness of the driver with high accuracy.

BRIEF DESCRIPTION OF DRAWINGS

FIG. 2 is a graph illustrating a distribution of proximity and an accelerator position generated in the driver condition determination device in FIG. 1, in which (a) is a distribution diagram and (b) is a graph obtained by origin-shifting the graph (a) around an average value.

DESCRIPTION OF EMBODIMENTS

Figure 1:
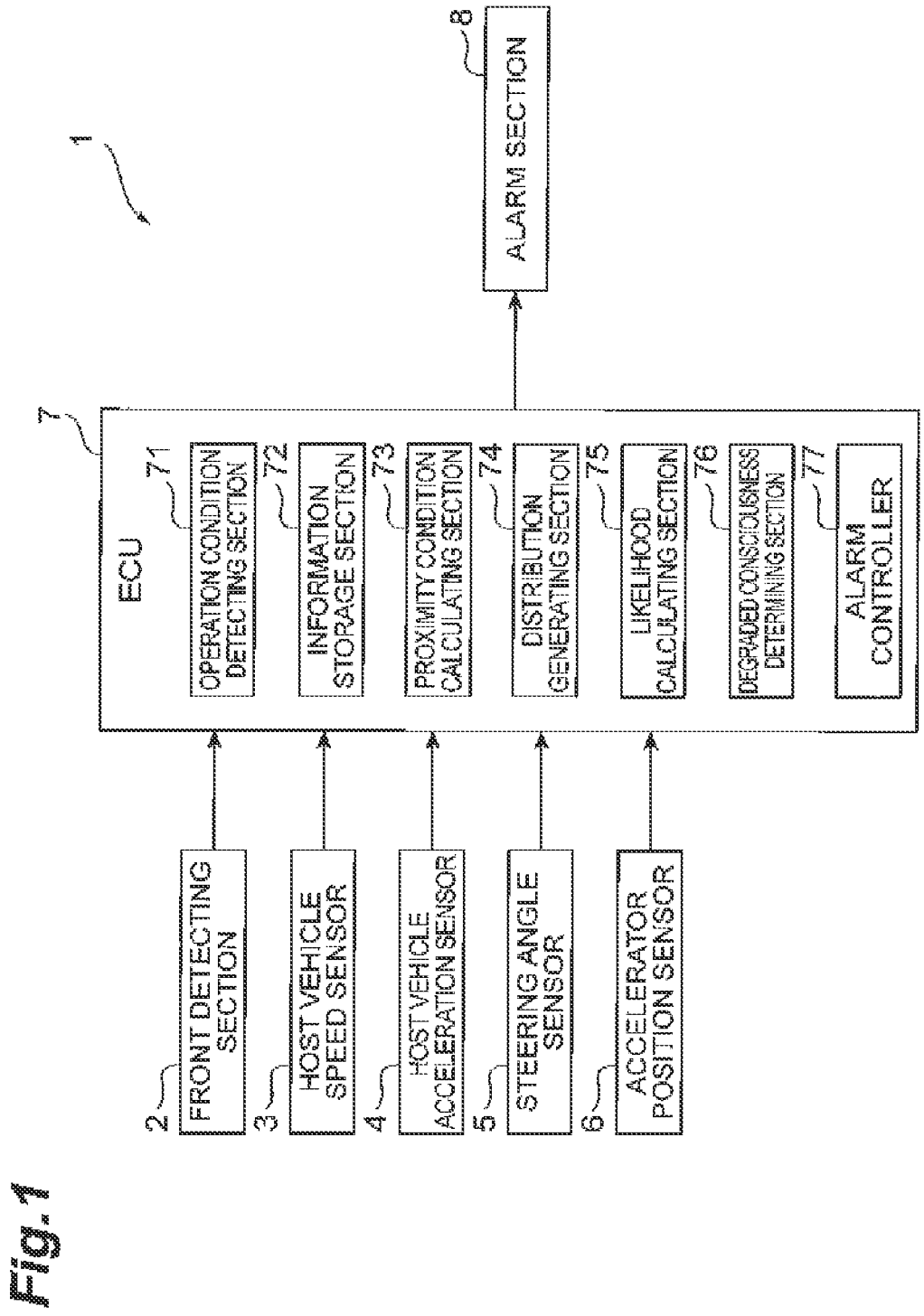
FIG. 1 is a block diagram illustrating a schematic configuration of a driver condition determination device according to an embodiment of the invention.

Hereinafter, embodiments of the invention will be described in detail with reference to the accompanying drawings. The same reference numerals are given to the same or equivalent elements, and description thereof will not be repeated.

FIG. 1 is a block diagram illustrating a schematic configuration of a driver condition determination device 1 according to an embodiment of the invention. The driver condition determination device 1 is mounted on a vehicle and determines whether a driver of the vehicle has degraded consciousness.

The driver condition determination device 1 includes a front detecting section 2, a host vehicle speed sensor 3, a host vehicle acceleration sensor 4, a steering angle sensor 5, an accelerator position sensor 6, an electronic control unit (ECU) 7, and an alarm section 8.

The front detecting section 2 detects the front of a host vehicle, and for example, employs a sensor that is attached to a front part of the vehicle, irradiates laser light to the front, and detects the presence or absence of a preceding vehicle by the reflected light. Further, the front detecting section 2 may be a camera that images the front of the host vehicle, for example. In this case, it is possible to use a captured image or video to detect the presence or absence of an obstacle and to detect a white line on a traveling lane. The front detecting section 2 is connected to the ECU 7, and an output signal thereof is input to the ECU 7.

The host vehicle speed sensor 3 functions as a vehicle speed detecting section that detects the speed of the host vehicle, and for example, employs a wheel speed sensor. The host vehicle speed sensor 3 is connected to the ECU 7, and an output signal thereof is input to the ECU 7.

The host vehicle acceleration sensor 4 functions as an acceleration detecting section that detects the acceleration of the host vehicle, an for example, employs an acceleration sensor that is installed to a front part of the host vehicle and detects a forward-backward acceleration and a lateral acceleration of the host vehicle. The host vehicle acceleration sensor 4 is connected to the ECU 7, and an output signal thereof is input to the ECU 7.

The steering angle sensor 5 functions as a steering angle detecting section that detects the steering angle of a steering wheel of the host vehicle. As the steering angle sensor 5, for example, a steering angle sensor that detects a rotation angle of a steering shaft is used. The steering angle sensor 5 is connected to the ECU 7, and an output signal thereof is input to the ECU 7. Instead of the steering angle sensor 5, a steering torque sensor may be used. In this case, the steering angle of the steering wheel is calculated on the basis of a steering torque value output by the steering torque. Further, any sensor other than the steering angle sensor 5 may be used as long as it is capable of obtaining the steering angle of the steering wheel.

The accelerator position sensor 6 functions as an acceleration position detecting section that detects the amount of pedaling (accelerator position) of an accelerator pedal. The accelerator position sensor 6 is connected to the ECU 7, and an output signal thereof is input to the ECU 7.

The ECU 7 is an electronic control unit that controls the entire device of the driver condition determination device 1, and includes a main computer that includes a central processing unit (CPU), a read only memory (ROM), and a random access memory (RAM), and an input signal circuit, an output signal circuit, and a power supply circuit, for example.

The ECU 7 includes at least an operation condition detecting section 71, an information storage section 72, a proximity condition calculating section 73, a distribution generating section 74, a likelihood calculating section 75, a degraded consciousness determining section 76, and an alarm controller 77.

The operation condition detecting section 71 detects an accelerating operation condition corresponding to the proximity of the vehicle to a preceding vehicle that is positioned in front of the vehicle. Here, the "accelerating operation condition" is used as a concept that includes conditions of a decelerating operation due to pedaling of a brake pedal, a steering wheel operation and the like, in addition to a simple accelerating operation of the vehicle. The operation condition detecting section 71 repeatedly obtains various signals output from the front detecting section 2, the host vehicle speed sensor 3, the host vehicle acceleration sensor 4, the steering angle sensor 5 and the accelerator position sensor 6, and stores the signals in the information storage section 72. Further, the operation condition detecting section 71 includes a function of calculating the steering speed on the basis of the signal input from the steering angle sensor 5, and a function of calculating the pedaling speed (accelerator pedaling speed) of the accelerator pedal on the basis of the signal input from the accelerator position sensor 6. The operation condition detecting section 71 stores the calculated steering speed and accelerator pedaling speed in the information storage section 72.

The proximity condition calculating section 73 calculates the proximity of the vehicle to the preceding vehicle that is positioned in front of the vehicle. The proximity condition calculating section 73 calculates the proximity to the preceding vehicle by first to fourth proximity condition calculating methods shown in the following description, for example, using various types of information stored in the information storage section 72. The proximity represents that the host vehicle is close to the preceding vehicle as the proximity is small and is distant from the preceding vehicle as the proximity is large. Hereinafter, the first to fourth proximity condition calculating methods will be described.

The first proximity condition calculating method is a method for calculating an inter-vehicle distance D between the host vehicle and the preceding vehicle detected by the front detecting section 2 to set the resultant as the proximity. Instead of the inter-vehicle distance D, a value obtained by performing a predetermined calculation such as four rules of arithmetic for the inter-vehicle distance D may be used as the proximity.

The second proximity condition calculating method is a method for using a time-to-collision (TTC) that is a physical quantity that indicates the degree of proximity of the host vehicle to the preceding vehicle. When a value of the time-to-collision (TTC) is large, the possibility of collision is low, and when the value is small, the possibility of collision is high. The time-to-collision (TTC) may be calculated by the following Expression (1).

[Expression 1]

$$TTC = D/Vr \quad (1)$$

In Expression (1), D represents the inter-vehicle distance, and Vr represents the relative speed of the host vehicle with respect to the preceding vehicle.

In the second proximity condition calculating method, the proximity condition calculating section 73 uses the time-to-collision (TTC) as the proximity. Instead of the time-to-collision (TTC), a value obtained by performing a predetermined calculation such as four rules of arithmetic for the time-to-collision (TTC) may be used as the proximity.

The third proximity condition calculating method is a method for using a time headway (THW) that is an index relating to time necessary for the host vehicle to reach the preceding vehicle. When a value of the time headway (THW) is large, the host vehicle is distant from the preceding vehicle, and when the value is small, the host vehicle is close to the preceding vehicle. The time headway (THW) may be calculated by the following Expression (2).

[Expression 2]

$$THW = D/Vs \quad (2)$$

In Expression (2), D represents the inter-vehicle distance, and Vs represents the vehicle speed of the host vehicle.

In the third proximity condition calculating method, the proximity condition calculating section 73 uses the time headway (THW) as the proximity. Instead of the time headway (THW), a value obtained by performing a predetermined calculation such as four rules of arithmetic for the time headway (THW) may be used as the proximity.

The fourth proximity condition calculating method is a method for using an index of perceptual risk estimate (PRE) that is an index that indicates a feeling (perceptual risk) that the host vehicle comes close to the preceding vehicle. When a value of the index of perceptual risk estimate (PRE) is large, the host vehicle is close to the preceding vehicle, and when the value is small, the host vehicle is distant from the preceding vehicle. The index of perceptual risk estimate (PRE) may be calculated by the following Expression (3).

[Expression 3]

$$PRE = (Vr + \alpha \cdot Vs + \beta \cdot Ax)/D^n \quad (3)$$

In Expression (3), Vr represents a relative speed, Vs represents the vehicle speed of the host vehicle, Ax represents a relative acceleration, D represents the inter-vehicle distance, $\alpha$ and $\beta$ are predetermined coefficients, and n is a predetermined positive real number of 1 or less.

In the fourth proximity condition calculating method, the proximity condition calculating section 73 uses an inverse number of the index of perceptual risk estimate (PRE) as the proximity. Further, a value obtained by performing a predetermined calculation such as four rules of arithmetic for the reciprocal of the index of perceptual risk estimate (PRE) may be used as the proximity. The index of perceptual risk estimate (PRE) may be used together with the above-mentioned inter-vehicle distance, the time-to-collision (TTC) and the time headway (THW). Further, since the index of perpetual estimate (PRE) has an excellent sensitivity compared with the inter-vehicle distance, the time-to-collision (TTC) and the time headway (THW), by using the index of perceptual risk estimate (PRE), it is possible to improve the determination accuracy of the degraded consciousness.

The proximity condition calculating section 73 calculates the proximity that indicates an index about how close the host vehicle is to the preceding vehicle using any one of the above-mentioned first to fourth proximity condition calculating methods. The proximity calculated by the proximity condition calculating section 73 is regularly or irregularly stored in the information storage section 72. Only the values obtained by the first to fourth proximity calculating methods are not necessarily used as the proximity, and values obtained by other methods may be used as the proximity.

The distribution generating section 74 generates the distribution that indicates the relationship between the proximity and the accelerating operation condition. The distribution generating section 74 creates the relationship between the proximity calculated by the proximity condition calculating section 73 and the accelerator position detected by the operation condition detecting section 71 as a graph shown in (a) of FIG. 2, and obtains an approximately straight line (y=ax+b) that is a main component. Here, the approximately straight line (y=ax+b) is obtained by the least-squares method. Specifically, when an approximate curve of n data points $(x_1, y_1)$, $(x_2, y_2), \ldots (x_n, y_n)$ is represented as y=ax+b, a and b may be calculated by using the following Expression (4) and Expression (5).

[Expression 4]

$$a = \frac{n \sum_{i=1}^{n} x_i y_i - \sum_{i=1}^{n} x_i \sum_{i=1}^{n} y_i}{n \sum_{i=1}^{n} x_i^2 - \left(\sum_{i=1}^{n} x_i\right)^2} \quad (4)$$

[Expression 5]

$$b = \frac{\sum_{i=1}^{n} x_i^2 \sum_{i=1}^{n} y_i - \sum_{i=1}^{n} x_i y_i \sum_{i=1}^{n} x_i}{n \sum_{i=1}^{n} x_i^{21} - \left(\sum_{i=1}^{n} x_i\right)^2} \quad (5)$$

An average $\epsilon$ of the distances from the obtained main component may be calculated using the following Expression (6).

[Expression 6]

$$\varepsilon = \frac{1}{n}\sum_{i=1}^{n}\left|\frac{y_i - (ax_i + b)}{\sqrt{a^2 + 1}}\right| \quad (6)$$

After calculation of the approximate curve (y=ax+b) that is the main component in the above method, the distribution generating section 74 shifts the average value of the obtained distribution to the origin, and rotates the data so that the main component is on the x axis, and a vertical component is on the y axis to create the graph shown in (b) of FIG. 2. Even though the origin shifting process is not performed, it is possible to perform the determination of the degraded consciousness of the driver using the following Expression (7), but by performing the origin shifting process, it is possible to easily perform the calculation and to simplify the likelihood calculation to be described later.

The likelihood calculating section 75 calculates a likelihood that indicates likelihood of the accelerating operation condition of the driver and a likelihood threshold value from the distribution (graph shown in (b) of FIG. 2) generated by the distribution generating section 74. The likelihood calculating section 75 calculates the likelihood of the accelerating operation condition of the driver by calculating a density function f(x, y) using an average $\mu_x$ and a population variance $\sigma_x$ of the main component and an average $\mu_y$ and a population variance $\sigma_y$ of the vertical component. The likelihood calculated by the likelihood calculating section 75 is used as the degree of normal traveling that indicates a normal accelerating operation condition (in consciousness) when the driver tailgates the preceding vehicle, and the likelihood threshold value is used as a threshold value of a gap between the accelerating operation condition of the driver and the normal accelerating operation condition. The likelihood calculating section 75 calculates the average $\mu_x$ and the population variance $\sigma_x$ of the main component, and the average $\mu_y$ and the population variance $\sigma_y$ of the vertical component from the distribution generated by the distribution generating section 74, and calculates the likelihood and the likelihood threshold value by the Gaussian mixture model (hereinafter, referred to as GMM). This calculation method will be described hereinafter.

The GMM is a technique that approximates data distribution by the sum of a plurality of normal distributions, and calculates the density function f(x, y) of two-dimensional distribution by the following Expression (7) using the average $\mu_x$ and the population variance $\sigma_x$ of the main component, the average $\mu_y$ and the population variance $\sigma_y$ of the vertical component and population covariance $\sigma_{xy}$, and uses the result as a normal traveling model.

[Expression 7]

$$f(x, y) = \frac{1}{2\pi\sigma_x\sigma_y\sqrt{1-\sigma_{xy}^2}}\exp\left[-\frac{1}{2(1-\sigma_{xy}^2)}\left\{\frac{(x-\mu_x)^2}{\sigma_x^2} + \frac{(y-\mu_y)^2}{\sigma_y^2} - \frac{2\sigma_{xy}(x-\mu_x)(y-\mu_y)}{\sigma_x\sigma_y}\right\}\right] \quad (7)$$

However, in the present embodiment, as described above, since the data is rotated so that the main component is on the x axis in the main component analysis, the population covariance $\sigma_{xy}$ becomes zero, and the likelihood calculating section 75 performs calculation of the likelihood only using $\mu_x$ and $\mu_y$, and the population variances $\sigma_x$ and $\sigma_y$. That is, the likelihood calculating section 75 calculates the density function f(x, y) of the second-dimensional formal distribution using the following Expression (8) in which $\sigma_{xy}=0$ in Expression (7).

[Expression 8]

$$f(x, y) = \frac{1}{2\pi\sigma_x\sigma_y}\exp\left[-\frac{1}{2}\left\{\frac{(x-\mu_x)^2}{\sigma_x^2} + \frac{(y-\mu_y)^2}{\sigma_y^2}\right\}\right] \quad (8)$$

Figure 3:
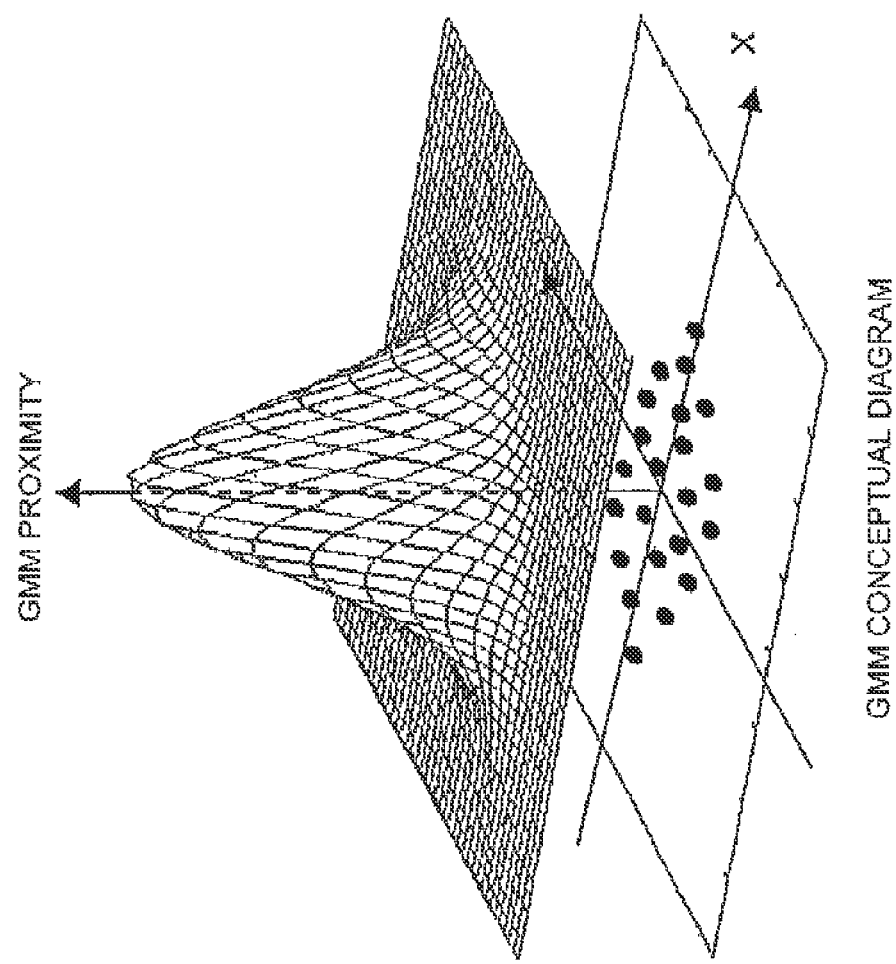
FIG. 3 is a graph illustrating a GMM likelihood obtained from the graph (b) of FIG. 2.

The likelihood calculating section 75 creates a model that uses a logarithm of the density function f(x, y) obtained as described above as a graph as shown in FIG. 3 in which the GMM likelihood is logarithmically increased as data is close to the average (origin) of the entire data, for example.

Further, the likelihood calculating section 75 approximates the obtained distribution by the normal distribution, and calculates the likelihood threshold value using the average (referred to as a likelihood average) and the variance (referred to as a likelihood variance), for example, by the following Expression (9).

[Expression 9]

Likelihood threshold value=likelihood average−m× likelihood dispersion (9)

In Expression (9), m represents a positive real number. By appropriately changing the value of m, it is possible to change the likelihood threshold value, and to change a determination threshold value of the degraded consciousness of the driver. Specifically, as m becomes large, the likelihood threshold value becomes small, and thus, it is possible to decrease the determination threshold value of the degraded consciousness, that is, to make it difficult to determine that the driver has the degraded consciousness. Further, as m becomes small, the likelihood threshold value becomes large, and thus, it is possible to increase the determination threshold value of the degraded consciousness, that is, to make it easy to determine that the driver has degraded consciousness.

When the gap between the accelerating operation condition of the driver detected by the operation condition detecting section 71 and the normal accelerating operation condition (in consciousness) exceeds a preset value, the degraded consciousness determining section 76 determines that the driver has the degraded consciousness. In other words, when the accelerating operation condition of the driver with respect to the proximity to the preceding vehicle deviates from the likelihood calculated by the likelihood calculating section 75, the degraded consciousness determining section 76 determines that the driver has the degraded consciousness. Specifically, when the likelihood of the accelerating operation condition of the driver detected by the operation condition detecting section 71 with respect to the proximity calculated by the proximity condition calculating section 73 is smaller than the likelihood threshold value calculated by the likelihood calculating section 75, the degraded consciousness determining section 76 determines that the driver performs a driving operation in non-consciousness and has the degraded consciousness. In a case where the likelihood of the accelerating operation condition of the driver is larger than the likelihood threshold value, the degraded consciousness determining section 76 determines that the driver performs a normal driving operation and is not in the degraded consciousness.

The alarm controller 77 controls the operation of the alarm section 8, and outputs an alarm control signal to the alarm section 8 in a case where it is determined that the driver has the degraded consciousness.

The above-described operation condition detecting section 71, the information storage section 72, the proximity condition calculating section 73, the distribution generating section 74, the likelihood calculating section 75, the degraded consciousness determining section 76 and the alarm controller 77 may be configured by individual hard ware, as long as their functions or processes can be performed.

The alarm section 8 gives an alarm to the driver of the vehicle, and is operated according to an alarm control signal output from the ECU 7. As the alarm section 8, an alarm section that gives an alarm to the driver through vision, hearing and touch may be used. For example, as the alarm section 8, a speaker, a buzzer, a navigation system monitor, a display, a lamp, an LED, a vibration device installed in a steering wheel or a seat, or the like may be used.

Next, an operation of the driver condition determination device 1 according to the present embodiment will be described.

Figure 4:
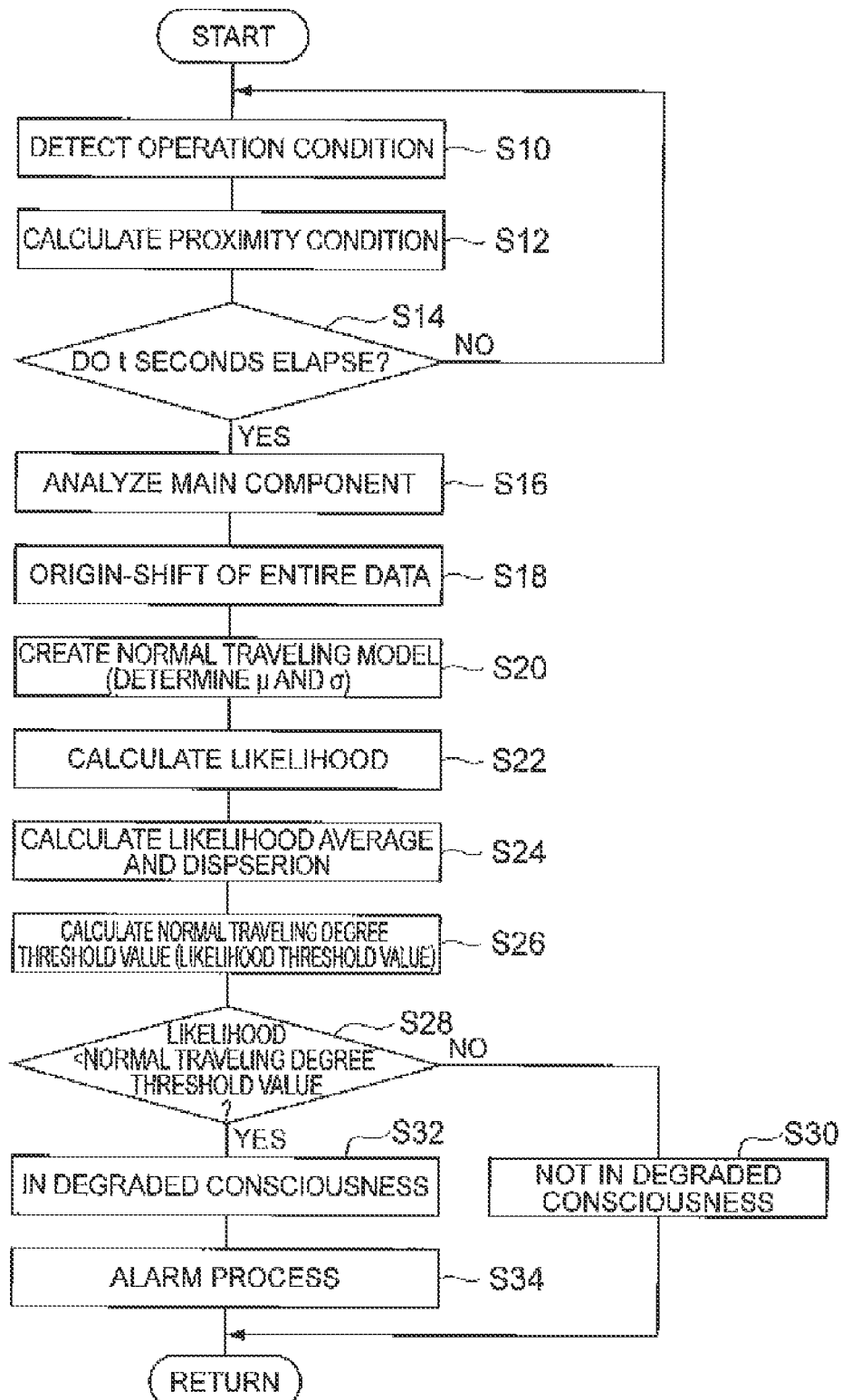
FIG. 4 is a flowchart illustrating an operation of the driver condition determination device in FIG. 1.

FIG. 4 is a flowchart illustrating an operation of the driver condition determination device 1. A series of control processes shown in the flowchart of FIG. 4 is repeatedly performed at a predetermined cycle by the ECU 7, for example.

The control process of the flowchart is started by ignition of the vehicle, for example. First, in step S10 (hereinafter, referred to as "S10", which is similarly applied to the other steps), an operation condition detection process is performed. The operation condition detection process is a process in which the operation condition detecting section 71 respectively obtains sensor signals included in output signals of the front detecting section 2, the host vehicle speed sensor 3, the host vehicle acceleration sensor 4, the steering angle sensor 5 and the accelerator position sensor 6 and stores the obtained sensor signals in the information storage section 72.

Then, the process moves on to S12, and a proximity condition calculation process is performed. The proximity condition calculation process is a process of calculating the proximity that indicates a proximity condition of the host vehicle to the preceding vehicle, and is performed by the proximity condition calculating section 73. Specifically, for example, as described above, the value of the inter-vehicle distance between the host vehicle and the preceding vehicle, the time-to-collision (TTC), the time headway (THW), the inverse number of the index of perceptual risk estimate (PRE), or the like is calculated as the proximity by the proximity condition calculating section 73.

Further, the process moves on to S14, and it is determined whether t seconds that are a predetermined time after the series of processes is started elapse or not. Further, in a case where t seconds do not elapse, the process returns to S10, and the operation condition detection process (S10) and the proximity condition calculation process (S12) are performed again. That is, until t seconds elapse, data sampling of the operation condition and the proximity is repeatedly performed, and the obtained data is used for the distribution generation and likelihood calculation to be described later. Further, in a case where it is determined that t seconds elapse in S14, the process moves on to S16.

In S16, a main component analysis process is performed by the distribution generating section 74. In the main component analysis process, the approximately straight line (y=ax+b) is generated from n data points $(x_1, y_1), (x_2, y_2), \ldots (x_n, y_n)$ that indicate the relationship between the accelerator position and the proximity obtained in S14, for example, using the least-squares method, that is, Expression (4) and Expression (5). The approximately straight line obtained in S14 is expressed as the graph shown in (a) of FIG. 2.

Then, the process moves on to S18, and an origin shifting process is performed by the distribution generating section 74. In the origin shifting process, the average value of distributions is shifted to the origin, and the data is rotated so that the main component is on the x axis and the vertical component is on the y axis, to thereby create the graph in (b) of FIG. 2, for example.

Then, the process moves on to S20, and a normal traveling model creation process is performed by the likelihood calculating section 75. The normal traveling model refers to a model of an accelerating operation condition of the driver in consciousness with respect to the proximity to the preceding vehicle, in which a different model is generated for each accelerating operation condition of the driver. Specifically, in S20, the likelihood calculating section 75 calculates the average $\mu_x$ and the population variance $\sigma_x$ of the main component and the average $\mu_y$ and the population variance $\sigma_y$ of the vertical component, and calculates the density function f(x, y) of the two-dimensional formal distribution by the above-mentioned Expression (8), to thereby generate the graph shown in FIG. 3, for example.

Then, the process moves on to S22, and a likelihood calculation process is performed by the likelihood calculating section 75. In S22, the likelihood calculating section 75 calculates the likelihood of a current accelerating operation condition of the driver using Expression (8). As the likelihood is increased, the driver performs the driving operation in a condition close to the normal condition, and as the likelihood is decreased, the driver performs the driving operation in a condition deviated from the normal condition.

Then, the process moves on to S24, and the likelihood distribution is approximated by the normal distribution to calculate the likelihood average and the likelihood variance. Then, the procedure moves on to S26, and the likelihood threshold value is calculated as a normal traveling degree threshold value using the likelihood average and the likelihood variance calculated in S24, and the above-mentioned Expression (9). The processes of S24 and S26 are performed by the likelihood calculating section 75.

Then, the process moves on to S28, and a determination process of determining the likelihood of the accelerating operation condition of the driver with respect to the current proximity stored in the information storage section 72 is performed. This determination process is performed by the degraded consciousness determining section 76. Specifically, it is determined whether the likelihood calculated in S22 is lower than the normal traveling degree threshold value calculated in S26, and in a case where the likelihood is equal to or higher than the normal traveling degree threshold value, the process moves on to S30, and in a case where the likelihood is lower than the normal traveling degree threshold value, the process moves on to S32.

In S30, the degraded consciousness determining section 76 determines that the driver is not in the degraded consciousness, and then, the series of processes is finished. In this case, for example, a flag for recognizing the degraded consciousness of the driver is turned off, and it is recognized by the flag that the driver is not in the degraded consciousness.

On the other hand, in S32, the degraded consciousness determination process is performed. The degraded consciousness determination process is a process of determining and recognizing that the driver has the degraded consciousness when the likelihood of the accelerating operation condition is lower than the normal traveling degree threshold value. In this case, for example, the flag for recognizing the degraded consciousness of the driver is turned on, and it is recognized by the flag that the driver has the degraded consciousness.

Then, the process moves on to S34, and an alarm process is performed. The alarm process is a process of outputting an alarm control signal to the alarm section 8. Through the alarm processes, the alarm section 8 performs an alarm operation for the driver. For example, the alarm section 8 gives sound or an alarm sound to the driver, provides an alarm display on a monitor or a display, or provides an alarm vibration to a steering wheel or a seat. Thus, the driver recovers consciousness from the degraded consciousness. If the process of S34 is finished, the series of control processes is finished.

As described above, according to the driver condition determination device according to the present embodiment, the operation condition detecting section 71 detects the accelerating operation condition corresponding to the proximity of the vehicle, and the degraded consciousness determining section 76 determines that the driver has the degraded consciousness when the gap between the accelerating operation condition of the driver and the normal accelerating operation condition (in consciousness) exceeds the preset value.

According to the driver condition determination device according to the present embodiment, since the degraded consciousness determination is performed when the gap between the accelerating operation condition of the driver and the normal accelerating operation condition exceeds the preset value, it is possible to grasp a characteristic of the normal driving operation (in consciousness) when the host vehicle tailgates the preceding vehicle, and to determine the degraded consciousness of the driver in consideration of the characteristic. Accordingly, it is possible to suppress an unnecessary alarm from being output due to a different driving operation for each driver when the host vehicle tailgates the preceding vehicle, and thus, it is possible to enhance the determination accuracy of the degraded consciousness of the driver.

Further, according to the driver condition determination device according to the present embodiment, the distribution generating section 74 generates the distribution that indicates the relationship between the proximity and the accelerating operation condition, and the likelihood calculating section 75 calculates the likelihood in the accelerating operation condition corresponding to the proximity and calculates the likelihood threshold value (normal traveling degree threshold value) as the predetermined set value, on the basis of the distribution condition. Accordingly, it is possible to model the characteristic of the accelerating operation condition for each driver when the host vehicle tailgates the preceding vehicle.

Further, according to the driver condition determination device according to the present embodiment, the likelihood calculating section 75 calculates the likelihood and the likelihood threshold value by the GMM. Accordingly, it is possible to model the accelerating operation condition for each driver with respect to the proximity with high accuracy, and to enhance the determination accuracy of the degraded consciousness of the driver.

Hereinbefore, the embodiment of the driver condition determination device according to the invention has been described, but the driver condition determination device according to the invention is not limited to the description of the present embodiment. The driver condition determination device according to the invention may be modified or may be used for other applications in a range without departing from the spirit of claims.

For example, in the above-described embodiment, an example in which the determination of the degraded consciousness of the driver is performed using the relationship between the accelerator position and the proximity is shown, but the accelerator position should not necessarily be used in the detection of the accelerating operation condition when the host vehicle tailgates the preceding vehicle. For example, the position of the brake pedal or the operation situation of the steering wheel may be used as the accelerating operation condition.

Further, in the above-described embodiment, an example in which the operation condition detecting section 71 repeatedly obtains various signals output from the front detecting section 2, the host vehicle speed sensor 3, the host vehicle acceleration sensor 4, the steering angle sensor 5 and the accelerator position sensor 6 and stores all the signals in the information storage section 72 is shown, but it is not necessary to repeatedly obtain all the signals. That is, necessary information such as an accelerator position may be obtained only as necessary, as long as the accelerating operation condition of the driver can be detected by the information.

Further, in the above-described embodiment, an example in which when the degraded consciousness determining section 76 determines that the driver has the degraded consciousness, the alarm is output to the driver from the alarm section 8 by the alarm controller 77 is shown, but the alarm controller 77 and the alarm section 8 should not necessarily be used. Specifically, when it is determined that the driver has the degraded consciousness, a deceleration process may be performed so that the host vehicle is separated from the preceding vehicle.

Further, in the above-described embodiment, an example in which the data sampling is performed for t seconds in S10 to S14 in the series of control processes shown in the flowchart in FIG. 4 and the main component analysis or the like is then performed every time is shown, but the process from the main component analysis to the likelihood threshold value calculation (from S16 to S26) may not be performed every time but may be performed whenever the driver is changed, for example. Further, the result of the data sampling may be stored in the information storage section 72 in advance. In this case, the processes from S10 to S26 may be omitted. That is, as long as the effects of the driver condition determination device according to the present embodiment can be obtained, some processes of the series of control processes in FIG. 4 may be omitted, or additional processes may be performed.

INDUSTRIAL APPLICABILITY

The invention may be used as a driver condition determination device that determines degraded consciousness of a driver of a vehicle.

Reference Signs List

1 . . . Driver condition determination device, 2 . . . Front detecting section, 3 . . . Host vehicle speed sensor, 4 . . . Host vehicle acceleration sensor, 5 . . . Steering angle sensor, 6 . . . Accelerator position sensor, 7 . . . ECU, 8 . . . Alarm section, 71 . . . Operation condition detecting section, 72 . . . Information storage section, 73 . . . Proximity condition calculating section, 74 . . . Distribution generating section, 75 . . . Likelihood calculating section, 76 . . . Degraded consciousness determining section, 77 . . . Alarm controller

The invention claimed is:

1. A driver condition determination device that determines whether a driver of a vehicle has degraded consciousness, comprising:
a proximity calculating section that calculates the proximity to a preceding vehicle positioned in front of the vehicle, using a proximity sense indicator that is an indicator that indicates a sense of proximity of the vehicle to the preceding vehicle;

an operation condition detecting section that detects an accelerating operation condition of the driver corresponding to the proximity of the vehicle to the preceding vehicle; and a degraded consciousness determining section that determines that the driver has the degraded consciousness when a gap between the accelerating operation condition of the driver detected by the operation condition detecting section and a normal accelerating operation condition exceeds a preset value, wherein the proximity sense indicator is calculated by the following Expression PRE $=(Vr + \alpha \cdot Vs + \beta \cdot Ax)/D^n$ and PRE represents the proximity sense indicator, Vr represents the relative speed of the host vehicle with respect to the preceding vehicle, Vs represents the vehicle speed of the host vehicle, Ax represents the relative acceleration of the host vehicle with respect to the preceding vehicle, D represents the inter-vehicle distance between the host vehicle and the preceding vehicle, Gt and β are predetermined coefficients, and n is a predetermined positive real number of 1 or less.

2. The driver condition determination device according to claim 1, further comprising:

a likelihood calculating section that calculates the likelihood of the accelerating operation condition of the driver and the preset value as a likelihood threshold value on the basis of the proximity to the preceding vehicle and a distribution state of the accelerating operation condition, wherein the degraded consciousness determining section determines that the driver has the degraded consciousness when the likelihood of the accelerating operation condition of the driver is lower than the likelihood threshold value.

3. The driver condition determination device according to claim 2, wherein the likelihood calculating section calculates the likelihood and the likelihood threshold value using a mixed normal distribution.

\* \* \* \* \*